(12) United States Patent
Sims

(10) Patent No.: US 7,491,189 B2
(45) Date of Patent: Feb. 17, 2009

(54) CATHETER INSERTION GUIDE

(76) Inventor: Brian Sims, 1289 49th Pl. South, Birmingham, AL (US) 35222

( * ) Notice: Subject to any disclaimer, the term of this patent is extended or adjusted under 35 U.S.C. 154(b) by 455 days.

(21) Appl. No.: 10/729,733

(22) Filed: Dec. 6, 2003

(65) Prior Publication Data

US 2004/0116860 A1 Jun. 17, 2004

Related U.S. Application Data

(60) Provisional application No. 60/431,578, filed on Dec. 6, 2002.

(51) Int. Cl.
*A61M 5/00* (2006.01)
(52) U.S. Cl. .................................................. 604/117
(58) Field of Classification Search ................. 604/250, 604/508, 117, 227–228
See application file for complete search history.

(56) References Cited

U.S. PATENT DOCUMENTS

| 4,326,516 | A | * | 4/1982 | Schultz et al. | 604/533 |
| 4,826,486 | A | * | 5/1989 | Palsrok et al. | 604/174 |
| 5,248,306 | A | * | 9/1993 | Clark et al. | 604/537 |
| 5,803,509 | A | * | 9/1998 | Adams | 285/114 |
| 6,827,705 | B2 | * | 12/2004 | Bierman | 604/180 |

* cited by examiner

*Primary Examiner*—Nicholas D Lucchesi
*Assistant Examiner*—Theodore J Stigell
(74) *Attorney, Agent, or Firm*—Darcell Walker

(57) ABSTRACT

The present invention system allows for an easier insertion and placement of IV catheters. This invention comprises a clip device attachable to a conventional catheter. The clip enables the practitioner to insert and withdraw the catheter device from the patient with the use of only one hand. This ability to perform this procedure with only one hand enables the practitioner to use the other free hand to hold, secure and restrain the patient. As a result, this invention greatly reduces the need to reinsert the needle multiple times because patient movement has affected the insertion process.

4 Claims, 4 Drawing Sheets

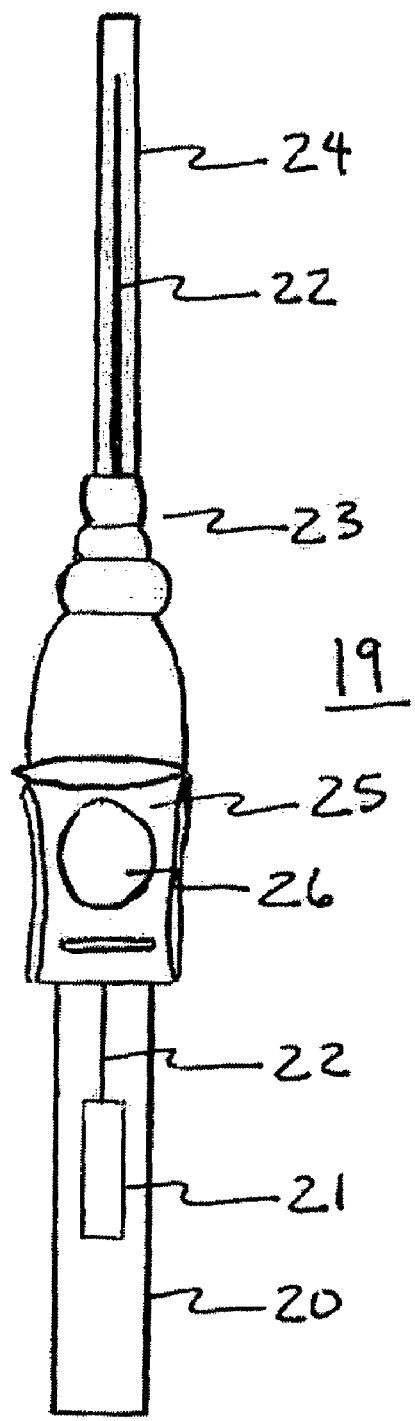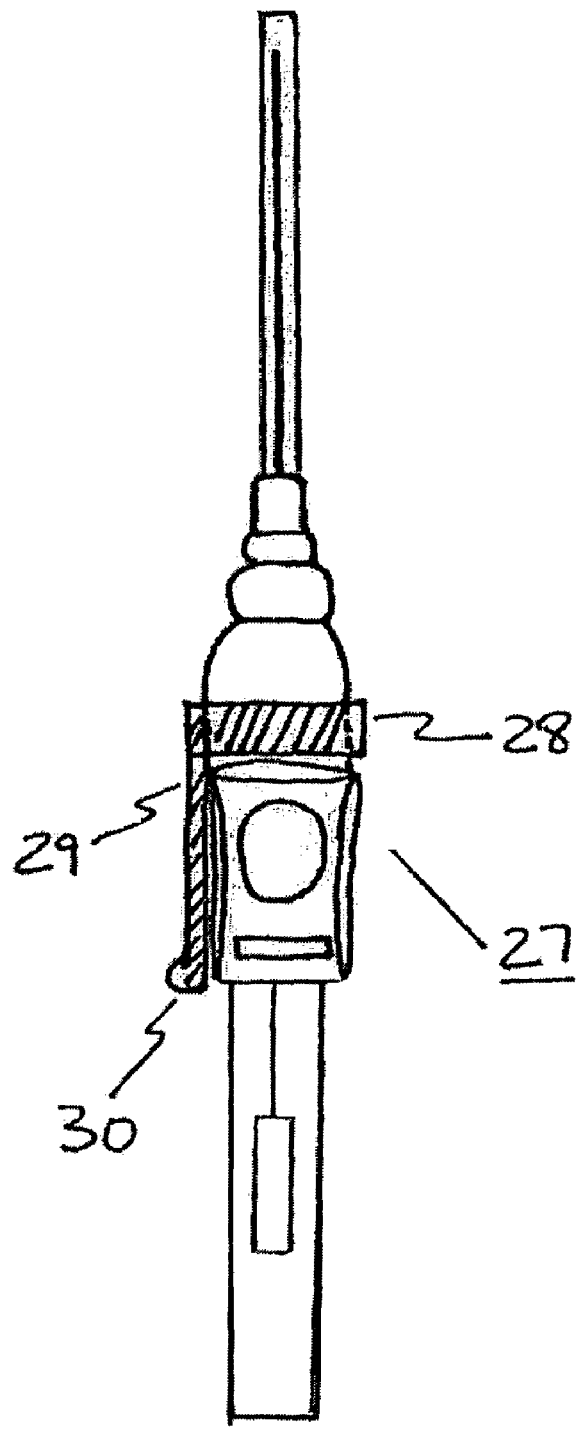
Figure 4
Figure 7

CATHETER INSERTION GUIDE

CROSS-REFERENCE TO RELATED APPLICATION

This application claims priority from provisional application No. 60/431,578, filed on Dec. 6, 2002, the contents of which are incorporated herein by reference.

FIELD OF THE INVENTION

This invention relates to a catheter device used to transfer fluids intravenously to and from a patient's body and in particular to a catheter device that has an attached guide that enables a practitioner to more easily maneuver the catheter during the process of inserting the catheter into a vein of a patient.

BACKGROUND OF THE INVENTION

Intravenous (IV) access in patients is a critical part of medical care. This access gives physicians/practitioners/nurses the ability to immediately administer and deliver medication to a patient. In emergency situations, IV access and delivery of the proper medication can save a patient's life. Therefore, in many cases, IV administration of fluids should be done as soon as possible.

IV administration of fluids is done via a catheter device. Although currently, there is widespread use of IV catheters, IV access using these catheters can be difficult. In practice, the process of IV placement and the related success of the placement vary from patient to patient. The pediatric patient presents a special challenge to IV placement because these patients and some adults do not like the thought or the feel of being stuck with a needle. Practitioners take great care to relieve any pain associated with a needle insertion by using various agents. However, many patients, usually age-dependent, do not appreciate or care for this procedure. Many factors affect the success of IV catheter placement and insertion in a child. Some of these factors include the size and course of the child's vein, the ability to keep the patient still during the insertion process, and the health professional's ability to efficiently insert the needle into the patient and float/advance the catheter into the vein of the patient. These variables cause IV catheter placement to be a difficult process that causes much stress for all parties involved, especially the patient.

The current models of IV catheters are sufficient for proper IV insertion when a patient is in a generally still position. However, when the patient is thrashing about, a simple IV insertion procedure can turn into a complicated procedure. One reason for the complication is because the patient's thrashing/movement will often require that the IV needle be repositioned in the patient one or more times. This repositioning process will generally require a health professional to reinsert the IV needle into the patient as many times as needed to get the IV needle in the proper position in the patient. Often times with a child, there may be several unsuccessful attempts at IV placement before the practitioner is successful. The level of skill of the health professionals that perform IV insertions is usually very high so the skill of the professional is normally not the reason for the unsuccessful IV attempts. The major factors in these unsuccessful IV insertion attempts are the movement of the patient and the inability to advance the catheter while a patient is moving. Combining these factors with the arduous task of placing a smaller catheter into a child's much smaller vein can make this procedure very difficult.

FIG. 1 shows a typical catheter section of a conventional angiocatheter device. This section comprises a flexible hollow tube 10 (known in the health care industry as the catheter) that is inserted into a patient's vessel. Initially this hollow tube (catheter) contains a needle. After insertion into the vein of the patient, the needle is withdrawn and thereby leaving the flexible catheter tube in the patient to supply fluids to the patient in an intravenous manner. A catheter base 11 contains one end of the catheter 10. Within the catheter base is a catheter housing 12 that actually contains the catheter end. This catheter housing has a hollow center that enables a needle to extend through the entire catheter section.

FIG. 2 is a conventional angiocatheter device shown in an expanded view. This angiocatheter has a catheter section 13 and a needle section 14. The catheter section 13 is the one illustrated in FIG. 1. The needle section has an internal housing 15, an external housing 16 and the needle 17 extending through both housings. A needle housing 18 contains the end of the needle. This needle housing is contained in the internal housing 15, but is attached to the external housing 16. The needle housing 18 connects to the external housing through a linear groove (not shown) in the internal housing. This groove runs along and completely through the external surface of the internal housing and enables the external housing 16 to move with respect to the internal housing 15. This movement of the external housing with respect to the internal controls the movement of the needle 17. FIG. 3 is an illustration of the angiocatheter illustrated in FIG. 2 in its normal configuration.

Another conventional angiocatheter design is shown in FIG. 4. This angiocatheter 19 has an outer housing 20 that contains an internal needle housing 21. Within the internal needle housing 21, is the needle 22 that is held in position in the needle housing by a spacer (not shown). The needle extends outward from the outer housing through the open end of the housing (upper end) attached to the catheter section 23. This extended portion of the needle is covered with a sheath 24. A pad 25 at the end of the upper end of the housing contains a button 26. Within the housing is a spring (not shown) that is attached to the internal needle housing 21. The other end of the spring attaches to the upper end of the outer housing and the needle 22. The spring is normally in an extended position. The button and spring serve as the retraction mechanism to retract the needle for removal after the insertion of the catheter into the patient's vessel. When the button is pressed, the extended spring is released and compresses. This compressing act retracts the needle from the catheter and patient and into the needle housing 21. Retraction of the needle leaves the catheter in the arm of the patient, as is the goal of the insertion procedure.

During the IV catheter insertion process, the health care practitioner follows these general steps:

1) Place a tourniquet on the patient's extremity to locate a vessel.
2) Prepare the patient's skin around the vessel area by wiping the location of the intended insertion with alcohol or other appropriate cleaning solution.
3) Remove the angiocatheter from the sterile package.
4) Hold the site (vessel area of the patient) secure: Practitioner holds the patient's arm or wrist; this step usually requires more than one person when the patient is a child.
5) Twist/Rotate the catheter to unlock; this step unlocks catheter section from needle section in either conventional angiocatheter design.
6) With the other hand, the practitioner finds a vein/vessel and inserts the needle.

7) When a flash of blood appears, the practitioner tries to advance/float the catheter into the vein.
8) The needle is retracted and placed in a sharp container
9) The practitioner flushes the catheter with fluid to determine if the catheter is in a good position.
10) Practitioner connects fluids to the catheter.

The main problem with the method for inserting the current IV catheter into the patient is that the advancement of the catheter in step 7 generally requires the practitioner to use both hands. This step requires the practitioner to remove their hand from holding the vein area secure, to holding the needle secure in the vein. The hand used to insert the needle is now to slide the lever to advance/float the catheter into the vein. During this time, if a patient, especially a child is moving, this movement commonly results in the needle pricking the side of the vein and thus making the vein unusable. In addition, the damaged vein requires the need to find another vein and begin the insertion process over from the beginning.

There remains a need for an IV catheter design that will enable a practitioner to hold an inserted needle in place and advance the catheter using only one hand for both tasks. A modification of the current catheter could be beneficial to patients, parents and health professional.

SUMMARY OF THE INVENTION

It is an object of the present invention to provide an angiocatheter device that will enable a practitioner to advance a catheter that has been inserted into a patient's vein.

Another objective of the present invention is to provide an angiocatheter in which the practitioner can advance the catheter using only one hand.

A third objective of the present invention is to provide an improved method to advance a catheter inserted into a patient's vein.

The present invention system allows for an easier placement of IV catheters. This invention comprises a clip device attachable to a conventional catheter as shown in FIG. 5. The clip enables the practitioner to insert and withdraw the catheter device from the patient with only one hand. This ability to perform this procedure with only one hand enables the practitioner to use the other free hand to hold and secure the patient's vein area and insertion site. As a result, this invention greatly reduces the need to reinsert the needle multiple times because patient movement has affected the insertion process.

The key benefit of this invention is that the clip enables the practitioner to move the catheter with one finger. In contrast, as shown in FIG. 4, the pad 25 used to move the catheter requires at least the use of the thumb and one finger. Since this use requires multiple fingers, the entire hand is necessary to move the catheter. The other hand is necessary to hold the catheter device in place while the catheter is being floated and subsequently, while the translation of movement of the needle with regard to the catheter is being provided. The present invention only requires the use of one finger to move the catheter and as a result, same hand can hold the needle during the insertion and removal process.

In the present invention, the practitioner would attach the clip to the catheter device. The practitioner would take the catheter and adjust the clip such that the catheter is in position for insertion into the patient. The practitioner would then hold/secure the patient's arm/wrist using one hand. During the insertion process, the practitioner would insert the needle into the vein. When flashing occurs (blood is seen), the practitioner would move the thumb or other finger of the hand holding the catheter to clip in a forward direction to advance the catheter into the vein. When the catheter has been inserted as desired, the practitioner can then retract the needle using the needle retraction button 26 or slide the external housing 16 away from the insertion site until a click is heard indicating that the needle has been securely retracted into the internal housing 15. This movement will withdraw the catheter from the patient and leave the flexible tube (catheter) in the patient's vein for the intravenous access.

DESCRIPTION OF THE DRAWINGS

FIG. 4 is an illustration of another conventional angiocatheter device.

FIG. 7 is an illustration of the present invention applied to the conventional angiocatheter device illustrated in FIG. 4.

DESCRIPTION OF THE INVENTION

Figure 5:
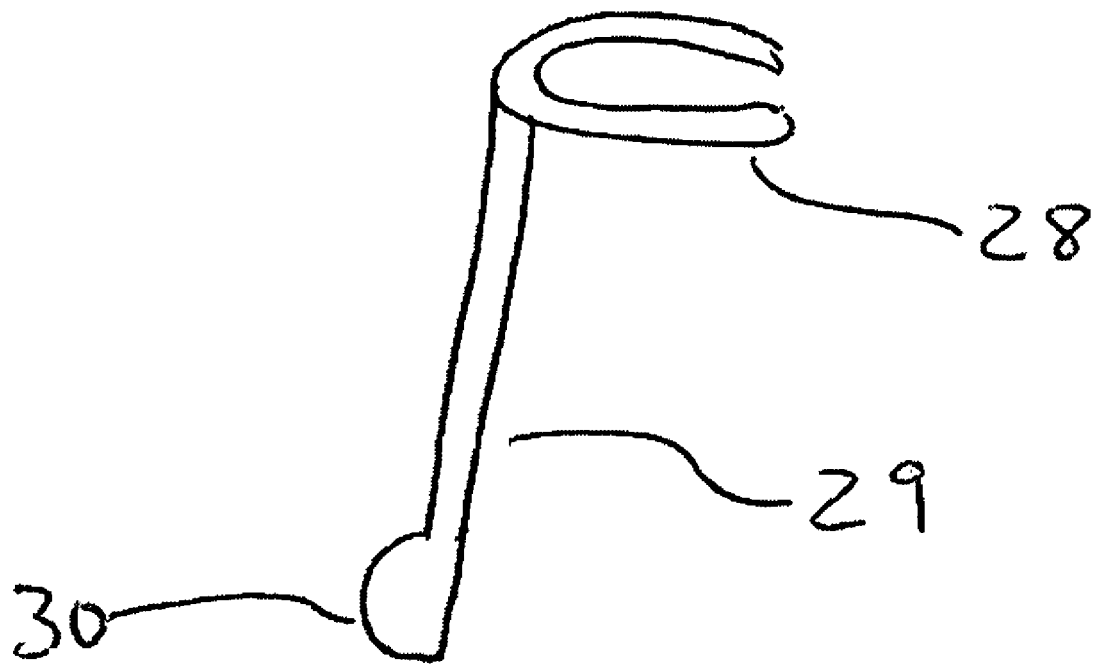
FIG. 5 is a side cross-section view of the clip of the present invention.
Figure 6:
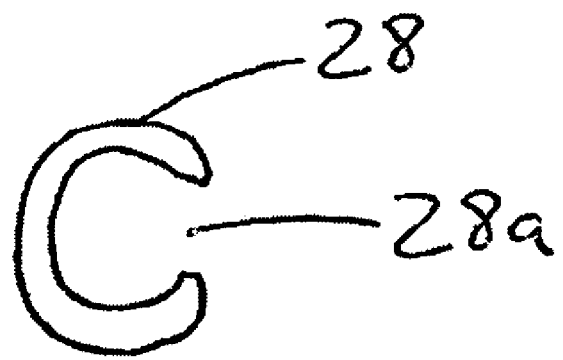
FIG. 6 is a top cross-section view of the clip of the present invention.

The present invention system allows for an easier placement of IV catheters. The present invention is a modification of a conventional angiocatheter used for insertion into the vein of a patient. Referring to FIG. 5, the present invention comprises a clip that attaches to the catheter. When the clip is attached to the catheter, a device is produced that provides for a substantially improved catheter insertion method. This mechanism can be described as a slide clip. The clip can be attached on either side of the catheter section. As shown in FIG. 6, the clip has a semi-circular section 28 that actually surrounds the catheter section and attaches the slide clip to the catheter base section 11. This section initially expands to engage the catheter at the opening 28a, which is smaller than the catheter. As the semi-circular section 28 encompasses the catheter, the section contracts to contain and secure the catheter base 11 inside the clip section 28. A linear section 29 of the slide clip extends from the circular section to a lip section 30. The lip section extends outward and enables the practitioner to easily engage this lip section. In the implementation of the invention, the practitioner can move the slide clip by applying pressure to the lip section 30 of the clip.

Figure 1:
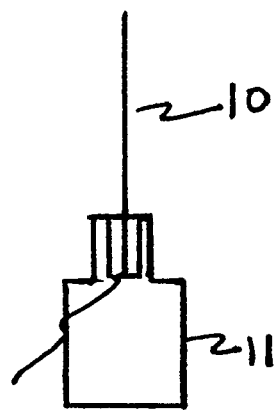
FIG. 1 is an illustration of the catheter section of a conventional angiocatheter device.
Figure 2:
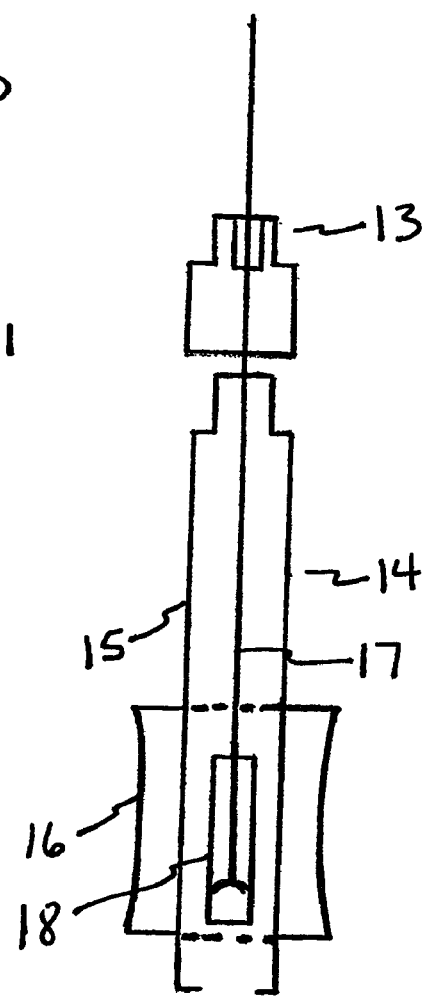
FIG. 2 is an expanded illustration of the component of a conventional angiocatheter device.
Figure 3:
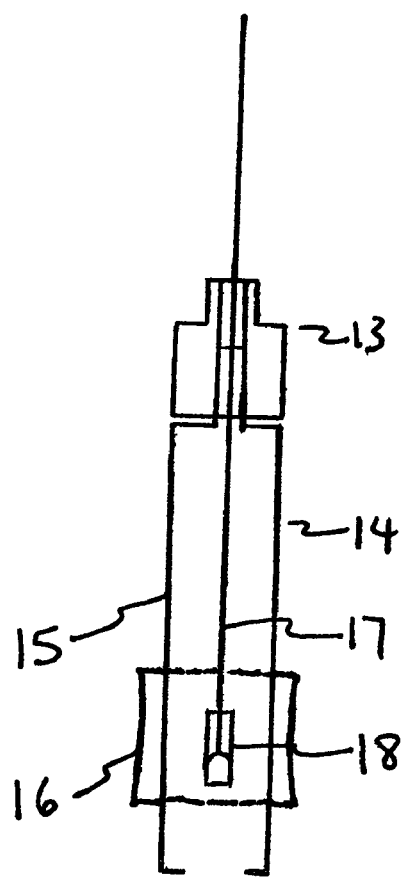
FIG. 3 is an illustration of the conventional angiocatheter device shown in FIG. 2.

The description of the present invention will be in reference to an application to the angiocatheter illustrated in FIG. 3 and FIG. 4. Referring to FIG. 7, on the side of the device is a sliding mechanism 27 that attaches to the catheter section. The side of the catheter can vary depending on whether the practitioner uses their right hand or left hand to hold the catheter. If the practitioner has the catheter in their left hand, the position of the clip could be on the right side of the catheter as shown in FIG. 7. In this application, the practitioner would insert the catheter into the vein of the patient in a conventional manner. At the point of flashing (blood seen), the practitioner could use their thumb to slide the clip 27 via the extension 30 such that the catheter tube is inserted into the patient. At the completion of the process, the practitioner could use their thumb to slide the clip and needle away from the insertion. While the practitioner uses their thumb to slide the clip 27 back and forth, the other fingers on the hand will continue to secure the catheter such that it does not move during this process.

In an alternate embodiment, the clip 27 can actually be attached to the catheter section 13 in FIG. 3 or 23 in FIG. 4. This embodiment may be more preferable when the instrument contains a spring that is used to internally withdraw the needle once the insertion is complete. In this case, the clip 27 will only be used for the insertion portion of the process.

In the present invention, attaching the slide clip to the catheter section will enable a practitioner to advance the catheter using the slide clip. In contrast to other methods, at the point that a blood return is seen, the practitioner can use the hand that inserted the needle into the vein to move the slide clip and advance the catheter into the patient's vein without having released the angiocatheter. The practitioner will use a finger from the hand holding the angiocatheter to advance the catheter into the vessel using one hand. The result of this technique is that the catheter is advanced using one hand and with minimal movement or change in patient position. Since the catheter at this point is unlocked from the angiocatheter, it will not be difficult to advance the catheter. In one method, the practitioner can use the lip section 30 to slide the clip and advance the catheter.

This sliding clip modification is necessary because one hand is usually placed on the infant to minimize movement and hold the site secure. The catheter base dislodges from the needle section of the catheter allowing for a one-handed delivery of the catheter.

Figure 8:
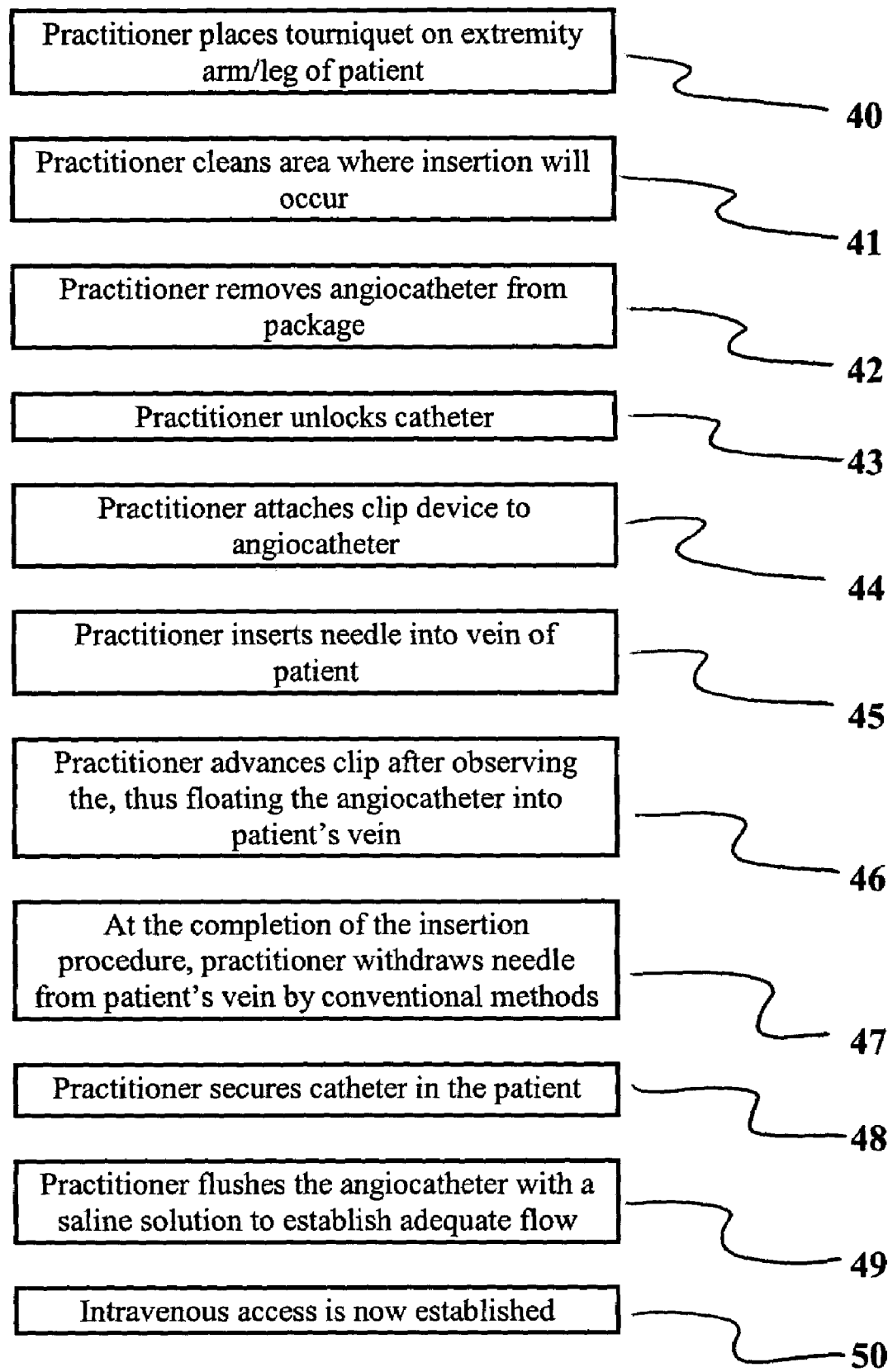
FIG. 8 illustrates the steps involved in using the modified angiocatheter in accordance with the present invention.

FIG. 8 illustrates the steps involved in using the modified angiocatheter in accordance with the present invention. The process has two phases: the preparation phase and the implementation phase. With regard to the preparation phase, as shown, step 40 places tourniquet on the extremity (arm/leg) of the patient in order to locate a blood vessel. Step 41 cleans the located area by wiping the location of the vessel with alcohol and allowing the location/site to dry. In step 42, the practitioner removes the angiocatheter from sterile package. Next, in step 43, the practitioner rotates the catheter in order to unlock the catheter. In step 44, the practitioner then attaches a clamp device (sliding clip) to the catheter base which allows for one-hand delivery of catheter using the thumb.

At this point, the process moves to the implementation phase. In step 45, the practitioner inserts the needle into the vein of the patient in a conventional manner. When flashing of the blood is seen, in step 46, the practitioner uses a finger or thumb to apply pressure to the sliding clip to advance the clip of the present invention. The advancement of the clip thus advances the catheter section into the vein using the attachment 27 of the present invention and the hand (preferably a finger or thumb). The practitioner uses the other fingers from this same hand to hold the catheter in place. At the completion of the insertion of the catheter section into the patient, the practitioner uses the same finger that advanced the catheter to retract the needle in step 47. This withdrawal process is similar to the insertion process of step 46 except the pressure to the sliding clip is to go in the direction away from the insertion. The next step 48 in the process is to secure the catheter in the patient with tape to prevent catheter movement. This securing process usually involves using tape to secure the catheter. The final step 49 is flushing the catheter with a saline solution to ensure that an adequate flow has been established. If flow is not sluggish, then adequate intravenous access has been established and is now ready for use.

The apparatus and methods of this invention provide significant advantages over the current art. The invention has been described in connection with its preferred embodiments. However, it is not limited thereto. Changes, variations and modifications to the basic design may be made without departing from the inventive concepts in this invention. In addition, these changes, variations and modifications would be obvious to those skilled in the art having the benefit of the foregoing teachings. All such changes, variations and modifications are intended to be within the scope of this invention.

I claim:

1. A method of inserting a catheter section of an angiocatheter device into a patient using a slide clip comprising the steps of:
   attaching the slide clip to the catheter section of the angiocatheter device, the slide clip comprising a catheter section engaging portion having a semi-circular portion configured to engage a portion of the catheter section, an extension section extending from the semi-circular portion and having two ends, a first end attached to the semi-circular portion and a second end at an opposite side of the extension section, and a lip section attached to the second end and configured to be engaged by a user of the device;
   unlocking an outer angiocatheter housing of the angiocatheter device in order to facilitate movement of the catheter section;
   establishing an initial insertion of the catheter section containing a needle into the patient until blood becomes visible; and
   using one hand, applying pressure to the slide clip in order to move the slide clip to further insert the catheter section into the patient.

2. The method as described in claim 1 further comprising after said pressure applying step, the step of using the same said one hand, applying pressure to the slide clip to withdraw the catheter section from the patient.

3. The method as described in claim 1 wherein said unlocking step further comprises rotating the outer angiocatheter housing to an unlock position.

4. A method of inserting a catheter section of an angiocatheter device into a patient using a slide clip comprising the steps of:
   attaching the slide clip to the catheter section of the angiocatheter device, the slide clip comprising a catheter section engaging portion having a semi-circular portion configured to engage a portion of the catheter section, an extension section extending from the semi-circular portion and having two ends, a first end attached to the semi-circular portion and a second end at an opposite side of the extension section, and a lip section attached to the second end and configured to be engaged by a user of the device;
   unlocking an outer angiocatheter housing of the angiocatheter device by rotating the outer angiocatheter housing in order to facilitate movement of an internal needle housing;
   establishing an initial insertion of the catheter section containing a needle into the patient until blood becomes visible; and
   using one hand, applying pressure to the slide clip in order to move the slide clip to further insert the catheter section into the patient.

* * * * *